United States Patent [19]

Knowles

[11] Patent Number: 4,528,990

[45] Date of Patent: Jul. 16, 1985

[54] APPARATUS FOR MEASURING HEAD AND SPINE MOVEMENT

[76] Inventor: Wayne C. Knowles, 3294 N. Elms Rd., Flushing, Mich. 48433

[21] Appl. No.: 508,033

[22] Filed: Jun. 27, 1983

[51] Int. Cl.³ ............................................... A61B 5/10
[52] U.S. Cl. ..................................... 128/782; 128/774
[58] Field of Search ................. 128/781, 782, 774; 33/174 D, 1 N

[56] References Cited

U.S. PATENT DOCUMENTS

| | | | |
|---|---|---|---|
| 1,590,499 | 6/1926 | Cozad | 128/782 |
| 2,565,381 | 8/1951 | Leighton | 33/221 X |
| 3,429,052 | 2/1969 | Hembd et al. | 33/220 |
| 3,465,450 | 9/1969 | Hamilton | 33/174 |

FOREIGN PATENT DOCUMENTS

| | | | |
|---|---|---|---|
| 736957 | 6/1980 | U.S.S.R. | 128/782 |
| 891065 | 12/1981 | U.S.S.R. | 128/774 |
| 904666 | 2/1982 | U.S.S.R. | 128/782 |
| 988275 | 1/1983 | U.S.S.R. | 128/774 |

OTHER PUBLICATIONS

Gilman et al., "Measurement of Head Movement", Behavior Res. Meth. & Inst., vol. 11 (1), pp. 37-41, Feb. 1979.

Primary Examiner—Edward M. Coven
Attorney, Agent, or Firm—Beaman & Beaman

[57] ABSTRACT

Head-mounted apparatus for measuring the movement of the spine or head about a substantially vertical axis, and also capable of indicating spine or head tilting. A headband firmly affixed to the head includes an indicia scale used in conjunction with a body reference indicator whereby the indicator is maintained stationary while the spine or head is rotated such that the relationship between the indicator and indicia scale represents rotative body movement. A gravity operated gauge also affixed to the apparatus measures tilting of the head with respect to the horizontal.

2 Claims, 4 Drawing Figures

APPARATUS FOR MEASURING HEAD AND SPINE MOVEMENT

BACKGROUND OF THE INVENTION

In the medical treatment of neck and spine problems it is often desired to be able to relatively accurately measure the movement of the head and spine for diagnostic and comparative purposes, particularly with respect to the cervical spine. Heretofore, apparatus for measuring spine movement has lacked accuracy and ease of use, and there is a need for low cost apparatus for accurately measuring head movements.

It is known to mount gravity sensitive gauges to the head for indicating head inclination, as shown in U.S. Pat. Nos. 2,565,381 and 3,429,052. Also, templates and reference scales have been used to determine the extent of head movement as shown in U.S. Pat. No. 3,465,450. Angle indicating devices of a protractor nature have also been used to show and measure pivotal movement of limb joints as disclosed in U.S. Pat. No. 1,590,499. However, apparatus for accurately measuring head movement, particularly about a vertical axis, is not readily available and the present invention provides apparatus filling a void in this area of the medical field.

It is an object of the invention to provide apparatus for measuring body movement wherein the movement of the head or spine about a vertical axis can be accurately determined.

A further object of the invention is to provide apparatus for measuring body movements which is economical to manufacture and distribute, and may be readily utilized by technicians of ordinary skill.

Yet a further object of the invention is to provide apparatus for measuring body movements about a vertical axis whereby restraining straps are employed to maintain consistency of head orientation during testing.

Another object of the invention is to provide apparatus for measuring body movements wherein rotation of the spine or head about a vertical axis is determined, and also, tilting of the head relative to the vertical may be indicated.

In the practice of the invention a headband is affixed to the head circumscribing the lateral portions thereof. A crown bridge mounted upon the headband extends over the crown of the head, and at its upper central portion a vertical shaft is mounted. A planar indicia scale is mounted upon the shaft having angular indications formed thereon whereby the scale will rotate as the body is turned about a substantially vertical axis. A body reference indicator is pivotally mounted upon the shaft and includes means, such as a pivoted end, for positioning adjacent a reference body part. Thus, by maintaining the indicator stationary rotation of the head causes relative movement between the indicator and the scale permitting measurement of head or spine movement.

Also, a gravity sensitive indicator is mounted upon the crown bridge shaft having a pendulum pivotally mounted about a horizontal axis whereby tilting of the head in a direction substantially aligned with the plane of pendulum movement will indicate the extent of body tilting upon a scale.

A chest band strapped about the patient may be used as a support for straps attached to the headband whereby the horizontal orientation of the head is maintained to assure uniformity of testing when rotating the head about a vertical axis. The apparatus of the invention may be used without the chest band and head straps, but such usage assures consistent results during successive tests.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
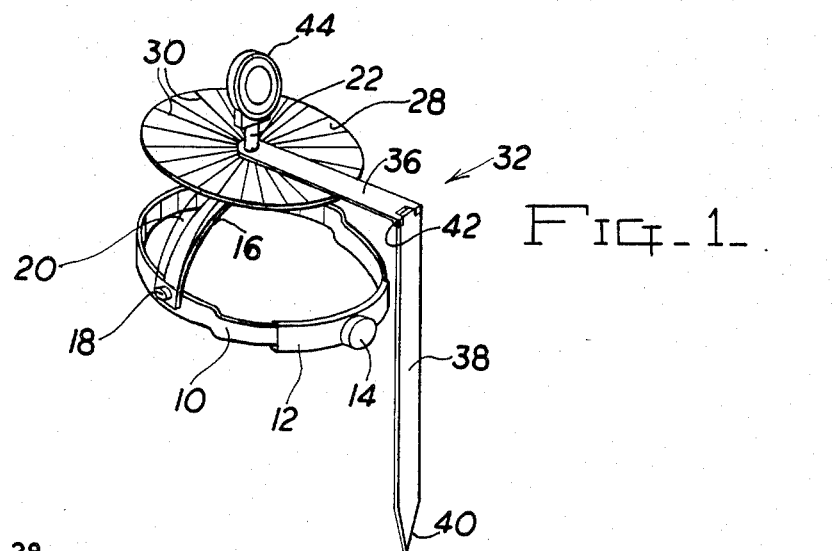
FIG. 1 is a perspective view of apparatus for measuring body movement in accord with the invention.

The apparatus of the invention will be appreciated from FIG. 1 wherein a headband is illustrated at 10. The headband is adapted to be placed upon the head and engage upon the lateral, front and rear portions of the head and the circumference of the headband is adjustable by adjustment means 12 which includes manually operated knob 14. The headband 10 may be of the conventional type used in welding helmets and the like, and by adjustment of the circumference by means of knob 14 the headband may be securely affixed to the wearer's head as apparent in FIGS. 2 and 3.

In the disclosed embodiment a bow 16 extends between the lateral sides of the headband and is affixed at its ends to the headband by connectors 18. The connectors 18 also support the crown bridge 20 superimposed over the bow 16, and at its upper central region the crown bridge supports the vertically disposed shaft 22. The shaft 22 includes an annular recess 24, FIG. 4, extending through the hole 26 defined in the crown bridge, and the shaft is affixed to the crown bridge in a nonrotative manner.

A circular indicia scale or protractor 28 is mounted upon the shaft 22 in a nonrotative manner, and the scale is provided with a plurality of radial lines 30 each bearing indicia indicating a portion of a circle, for instance, 10°. The radial lines are designated by appropriate degree legends.

A body reference indicator 32 is pivotally mounted upon the shaft 22 above the indicia scale 28 by means of recessed bearing portion 34 defined upon the shaft, and the body reference indicator is capable of freely rotating upon the shaft relative to the scale. In the disclosed embodiment the indicator 32 consists of the inner portion 36 rotatively mounted upon the shaft 22, and the outer portion 38. These portions are interconnected with a hinge pin 42 whereby the outer portion 38 is pivotally connected to the inner portion permitting the outer portion pointer end to be disposed adjacent the desired body reference point. It is to be appreciated that in use, the flat scale 28 will be disposed in a substantially horizontal plane, while the shaft axis will be vertical, and the axis of hinge 42 will be disposed at right angles with respect to the length of outer portion 38, and lie in a horizontal plane.

Figure 4:
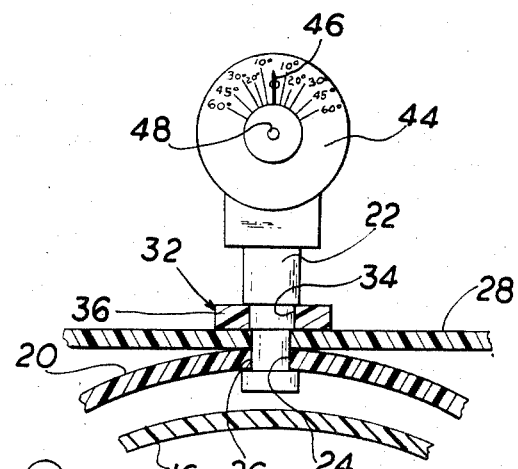
FIG. 4 is an enlarged, detailed, partially sectioned view of the crown bridge shaft and associated components.

Preferably, a gravity operated angle gauge 44 is rotatably attached to the upper end of the shaft 22, and this angle gauge may be of known design including a pendulum-indicator 46 pivotally mounted upon a horizontal pivot axis as represented at 48, FIG. 4. Indicia is defined upon the gauge adjacent the indicator 46, and because of the influence of gravity upon the indicator pendulum of the gauge tilting of the gauge relative to the vertical will cause the indicator to specify a particular angle of tilting. Of course, with respect to the gauge 44, angle deviations are sensed that are in the plane in which the gauge pendulum swings.

Figure 2:
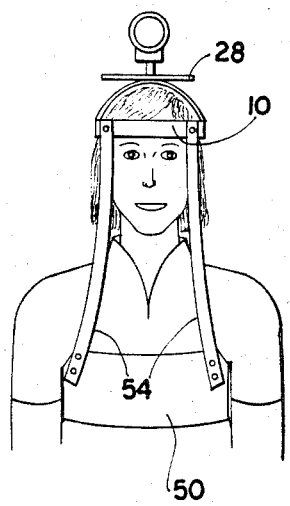
FIG. 2 is a front view of the apparatus as worn by a patient, the chest band being illustrated.
Figure 3:
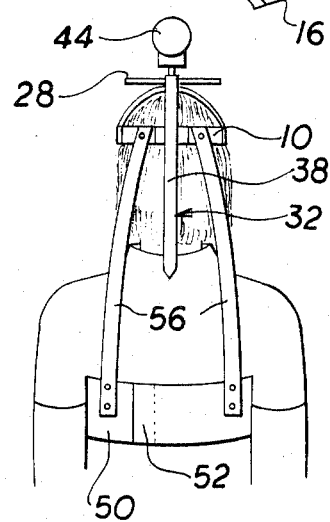
FIG. 3 is a rear view of the apparatus as used with the chest band.

A chest band 50 may encompass the wearer's chest and back, FIGS. 2 and 3, and is adjustably closed by fasteners 52 such as represented in FIG. 3, which may be of the Velcro type, or laces and buckles could be employed. A plurality of anterior straps 54 and posterior straps 56 are attached to the chest band extending to the headband 10 as will be appreciated from FIGS. 2 and 3, and the purpose of the straps is to restrain the head against tilting relative to the vertical. Thus, the chest band and straps are primarily employed when checking the patient's spine or head relative to rotation about the vertical axis, and the straps do not impede such orientation. The straps are taut enough to stabilize the cervical area to permit examination of the range of motion of the lumbar thoracic spine. It is to be understood that the use of the chest band and straps is optional.

When firmly mounted upon the patient's head, the pointer end 40 of the body reference indicator 32 will be located adjacent a body reference point, usually the lower spine, and the patient will be asked to rotate their upper body or head in either direction. Such body rotation will cause the scale 28 to rotate relative to the indicator 32 which is maintained in stationary relationship to the wearer's spine, and in this manner the rotative body movement is readily determined indicating the range of motion to which the applicant's spine or head may be turned.

When it is desired to check the ability of the wearer to tilt the head in a lateral direction the angle gauge 44 will be observed as tilting occurs, and the range of motion observed. By rotating the gauge 44 90° on shaft 22 the gauge may be used to check extension, anterior flexion, and left and right lateral flexion.

By the use of the apparatus of the invention the degree of rotation of the cervical spine may be accurately determined, and progressive patient conditions can be accurately monitored since during each use the indicator pointer end 40 may be accurately maintained at the same position relative to the patient's spine and consistent results will be obtained over an extended duration. When measuring the range of motion of the spine, it is desirable that the head not rotate relative to the neck and upper spine as the torso is twisted and the chest band and straps are helpful in this regard. However, it is also possible to use a cervical collar to fix the head relative to the body when using the invention.

It is appreciated that various modifications to the inventive concepts may be apparent to those skilled in the art without departing from the spirit and scope of the invention.

I claim:

1. Apparatus for measuring rotative body movement about a substantially vertical axis comprising, in combination, a headband adapted to be securely attached to the head comprising a band adapted to encircle the lateral portions of the patient's head an adjustable means defined on said band for varying the circumference thereof, a crown bridge mounted upon said headband for extending over the crown of the head, an indicia scale fixedly mounted upon said crown bridge adapted to lie in a substantially horizontal plane having a centrally located pivot shaft defining a pivot axis, said scale lying in a plane perpendicular to said pivot axis, a body reference indicator pivotally mounted upon said crown bridge at said pivot shaft for rotation about a substantially vertical axis disposed adjacent said scale, said body reference indicator comprising an elongated member having a first portion pivotally mounted upon said crown bridge at said pivot shaft and disposed adjacent said indicia scale and a second portion hinged to said first portion by a hinge axis substantially perpendicular to the length of said first portion whereby said second portion may pivot downwardly toward the wearer's body for positioning relative thereto whereby upon said body reference indicator being maintained at a predetermined location relative to the patient's body rotation of the patient's head about a substantially vertical axis will rotate said scale with respect to said indicator permitting determination of the extent of the patient's head movement, and a gravity operated gauge mountable upon said pivot shaft indicating the inclination of said pivot shaft to the vertical.

2. Apparatus for measuring rotative body movement as in claim 1, a chest band adapted to encircle the patient's chest, and a plurality of restraint straps extending from said chest band to said headband restraining tilting of the head relative to the vertical.

* * * * *